(12) United States Patent
Klein et al.

(10) Patent No.: US 8,691,284 B2
(45) Date of Patent: Apr. 8, 2014

(54) FLUORINATED BLOCK CO-POLYMERS

(75) Inventors: Josef Peter Klein, Vashon, WA (US);
Floyd Brian Karp, Seattle, WA (US);
Yansong Gu, Bellevue, WA (US); Roger Alan Sahm, Snohomish, WA (US);
Luisa Mayorga Szott, Seattle, WA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/443,576

(22) Filed: Apr. 10, 2012

(65) Prior Publication Data
US 2013/0011487 A1 Jan. 10, 2013

(30) Foreign Application Priority Data
Jul. 7, 2011 (WO) ............... PCT/US2011/043138

(51) Int. Cl.
*A61K 33/00* (2006.01)
*C12N 5/07* (2010.01)
*A61P 17/02* (2006.01)
*A61P 7/00* (2006.01)

(52) U.S. Cl.
USPC ............ 424/600; 525/427; 525/182; 435/375

(58) Field of Classification Search
USPC .................... 424/600; 525/427, 182; 435/375
See application file for complete search history.

(56) References Cited

U.S. PATENT DOCUMENTS

| 7,399,860 | B2 | 7/2008 | Kumar et al. |
| 2004/0208845 | A1 | 10/2004 | Michal et al. |
| 2006/0002881 | A1 | 1/2006 | Peng et al. |
| 2010/0055067 | A1 | 3/2010 | Park |

FOREIGN PATENT DOCUMENTS

| JP | 2010-138137 | * | 6/2010 | ............. A61K 9/107 |
| WO | WO-03/082303 | | 10/2003 | |
| WO | WO-2006/003731 | | 1/2006 | |
| WO | WO-2008/071957 | | 6/2008 | |
| WO | WO-2010/077671 | | 7/2010 | |

OTHER PUBLICATIONS

Pitarresi et al., Fluorinated Derivatives of a Polyaspartamide bearing polyethylene glycol chains as oxygen carriers, 2008, J. Fluorine Chem., 129, 1096-1103.*
Chang, E. et al., "Tissue engineering using autologous microcirculatory beds as vascularized bioscaffolds," The FASEB Journal, 2009, vol. 23, pp. 906-915.
Chin, K, et al., "Hydrogel-perfluorocarbon composite scaffold promotes oxygen transport to immobilized cells," Biotechnol Prog, 2008, vol. 24, pp. 358-366.
Dou, H., et al., "Synthesis and purification of mono-PEGylated insulin," 2007, Chem Biol Drug Res 69, pp. 132-138.
Du, W. et al., "Synthesis, Characterization, and Aqueous Self-Assembly of Amphiphilic Poly(ethylene oxide)-Functionalized Hyperbranched Fluoropolymers," Journal of Polymer Science: Part A: Polymer Chemistry, 2010, vol. 48, pp. 3487-3496.
Fast, J.P., et al., "Fluoropolymer-based emulsions for the intravenous delivery of sevoflurane," Anesthesiology, Oct. 2008, vol. 109, No. 4, pp. 651-656.
Khattak, S.F., et al., "Enhanced oxygen tension and cellular function in alginate cell encapsulation devices through the use of perfluorocarbons," Biotech Bioengineering, Jan. 1, 2007, vol. 96, No. 1, pp. 156-166.
Kim, H.W., et al., "Artificial oxygen carriers as red blood cell substitutes: a selected review and current status," Artificial Organs, 2004, vol. 28, No. 9, pp. 813-828.
Kinstler, O., et al., "Mono-N-terminal poly(ethylene glycol)-protein conjugates," Adv Drug Deliv Rev, 2002, vol. 54, pp. 477-485.
Krafft, M.P., "Fluorocarbons and fluorinated amphiphiles in drug delivery and biomedical research," Advanced Drug Delivery Reviews, 2001, vol. 47, pp. 209-228.
Pitarresi, G., et al., "Fluorinated derivatives of a polyaspartamide bearing polyethylene glycol chains as oxygen carriers," Journal of Fluorine Chemistry, Nov. 2008, vol. 129, No. 11, pp. 1096-1103.
Radisic, M., et al., "Biomimetic approach to cardiac tissue engineering: oxygen carriers and channeled scaffolds," Tissue Enginnering, Nov. 8, 2006, vol. 12, pp. 2077-2091, 2 pages.
Weinman, C.J., et al., "Antifouling block copolymer surfaces that resist settlement of barnacle larvae," 2007, PMSE Preprints 96, pp. 597-598.
International Search Report for Intl. Pat. Appln. No. PCT/US2011/043138, mailed on Aug. 26, 2011, 4 pp.
Stevens, K.R., et al., "Physiological function and transplantation of scaffold-free and vascularized human cardiac muscle tissue," Proceedings of the National Academy of Sciences, 2009, vol. 106, No. 39, pp. 16568-16573.
Tsunoda, S., et al., "Molecular design of polyvinylpyrrolidone-conjugated interleukin-6 for enhancement of in vivo thrombopoietic activity in mice," Journal of Controlled Release, 2000, vol. 68, pp. 335-341.

* cited by examiner

*Primary Examiner* — Anoop Singh
*Assistant Examiner* — Anna Falkowitz
(74) *Attorney, Agent, or Firm* — Foley & Lardner LLP

(57) ABSTRACT

A block co-polymer includes a water soluble carrier block; an amino acid-based or acrylic acid-based block; and the amino acid-based or acrylic acid-based block includes a fluorinated alkyl group or a fluorinated alkylene glycol group.

6 Claims, 2 Drawing Sheets

US 8,691,284 B2

FLUORINATED BLOCK CO-POLYMERS

CROSS-REFERENCE TO RELATED APPLICATIONS

This application claims the benefit of International Application Serial No. PCT/US2011/043138, filed on Jul. 7, 2011, the entire disclosure of which is hereby incorporated by reference for all purposes in its entirety as if fully set forth herein.

FIELD

The present technology relates fluorinated block co-polymers for oxygen transport.

BACKGROUND

The following description is provided to assist the understanding of the reader. None of the information provided or references cited is admitted to be prior art to the present technology.

Successful implantation of engineered tissues has thus far been limited to thin tissue constructs. A major challenge for the successful implantation of thick tissues is the limited access of diffusible oxygen and nutrients to cells in the core of the implant leading to necrotic death of these cells. Oxygen depletion is a major factor responsible for this core cell death. To counteract oxygen depletion in the tissue core agents such as vascular endothelial growth factor (VEGF) have been added to engineered tissues to promote tissue vascularization. Unfortunately, even in the presence of growth factors like VEGF in situ vascularisation of engineered tissues is a relatively slow process; too slow to prevent formation of a necrotic core.

SUMMARY

In one aspect, a block co-polymer is provided including a water soluble carrier block; an amino acid-based or acrylic acid-based block; and the amino acid-based or acrylic acid-based block includes a fluorinated alkyl group or a fluorinated alkylene glycol group. In some embodiments, the block co-polymer is represented by Formula I:

Block A-L-Block B    (I)

where Block A is the water soluble carrier block; Block B is the amino acid-based or acrylic acid-based block; and L is a linker group between Block A and Block B.

In another aspect, a method of providing oxygen to tissues includes contacting the block co-polymer above with oxygen, and forming oxygenated micelles in an aqueous environment; and contacting the oxygenated micelles with tissue.

In another aspect, a composition includes oxygenated micelles including a block co-polymer above, molecular oxygen; and an aqueous vehicle.

In another aspect, a method includes contacting the composition of the oxygenated micelles with cardiac, hepatic and renal tissue.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1:
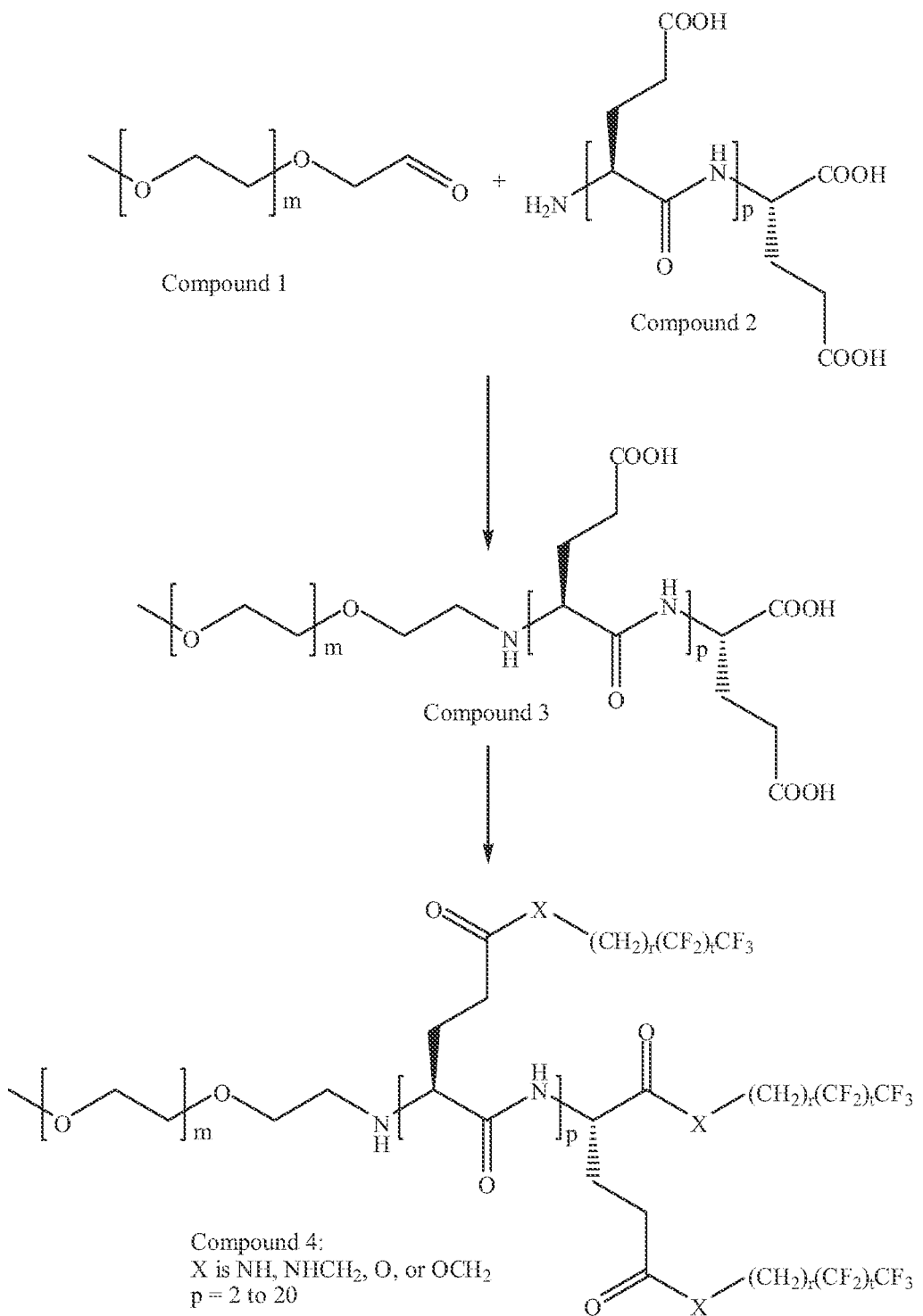
FIG. 1 is a schematic illustration of the synthesis of Compound 4, according to the examples.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. In some embodiments, the alkyl groups may be substituted alkyl groups.

Cycloalkyl groups are cyclic alkyl groups having from 3 to 10 carbon atoms. In some embodiments, the cycloalkyl group has 3 to 7 ring members, whereas in other embodiments the number of ring carbon atoms range from 3 to 5, 3 to 6, or 5, 6 or 7. Cycloalkyl groups further include monocyclic, bicyclic and polycyclic ring systems. Monocyclic groups include, e.g., cyclopropyl, cyclobutyl, cyclopentyl, cyclohexyl, and cycloheptyl groups. Bicyclic and polycyclic cycloalkyl groups include bridged or fused rings, such as, but not limited to, bicyclo[3.2.1]octane, decalinyl, and the like. Cycloalkyl groups include rings that are substituted with straight or branched chain alkyl groups as defined above. In some embodiments, the cycloalkyl groups are substituted cycloalkyl groups. Representative substituted alkenyl groups may be mono-substituted or substituted more than once, such as, but not limited to, mono-, di- or tri-substituted with substituents such as those listed above. Representative substituted alkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Thus, alkenyl groups have from 2 to 24 carbon atoms, and typically from 2 to 10 carbons or, in some embodiments, from 2 to 8, 2 to 6, or 2 to 4 carbon atoms. Examples include, but are not limited to vinyl, allyl, —CH=CH(CH$_3$), —CH=C(CH$_3$)$_2$, —C(CH$_3$)=CH$_2$,  —C(CH$_3$)=CH(CH$_3$), —C(CH$_2$CH$_3$)=CH$_2$, among others.

Representative substituted alkenyl groups may be mono-substituted or substituted more than once, such as, but not limited to, mono-, di- or tri-substituted with substituents such as those listed above.

The terms "alkylene," "cycloalkylene," and "alkenylene," alone or as part of another substituent means a divalent radical derived from an alkyl, cycloalkyl, or alkenyl group, respectively, as exemplified by —CH$_2$CH$_2$CH$_2$CH$_2$—. For alkylene, cycloalkylene, and alkenylene linking groups, no orientation of the linking group is implied.

The term "amine" (or "amino") as used herein refers to —NHR and —NRR' groups, wherein R, and R' are independently hydrogen, or a substituted or unsubstituted alkyl, alkenyl, alkynyl, cycloalkyl, aryl or aralkyl group as defined herein. Examples of amino groups include —NH2, methylamino, dimethylamino, ethylamino, diethylamino, propylamino, isopropylamino, phenylamino, benzylamino, and the like.

The term "oxo" refers to a divalent oxygen group. While the term includes doubly bonded oxygen, such as that found in a carbonyl group, as used herein, the term oxo explicitly includes singly bonded oxygen of the form —O— which is part of a polymer backbone. Thus, an oxo group may be part of an ether linkage (—O—), an ester linkage (—O—C(O)—), a carbonate linkage (—O—C(O)O—), a carbamate linkage (—O—C(O)NH— or —O—C(O)NR—), and the like.

"Substituted" refers to a chemical group as described herein that further includes one or more substituents, such as lower alkyl (including substituted lower alkyl such as haloalkyl, hydroxyalkyl, aminoalkyl), aryl (including substituted aryl), acyl, halogen, hydroxy, amino, alkoxy, alkylamino, acylamino, thioamido, acyloxy, aryloxy, aryloxyalkyl, carboxy, thiol, sulfide, sulfonyl, oxo, both saturated and unsaturated cyclic hydrocarbons (e.g., cycloalkyl, cycloalkenyl), cycloheteroalkyls and the like. These groups may be attached to any carbon or substituent of the alkyl, alkenyl, alkynyl, aryl, cycloheteroalkyl, alkylene, alkenylene, alkynylene, arylene, hetero moieties. Additionally, the substituents may be pendent from, or integral to, the carbon chain itself.

Provided herein is a means to provide oxygen to tissues thereby promoting cell survival and/or preventing, or ameliorating, cell or tissue damage and/or death. In some embodiments, this may be used in tissues during for example the time period between tissue implantation or transplantation and vascularisation, or during culture of multilayer tissue in vivo. Such tissues may include engineered tissues and transplant tissue. Block co-polymers are provided which can transport the oxygen to the tissues. The block co-polymers include blocks of a water soluble polymer component covalently bound to blocks of polypeptide that are attached to oxygen-carrying polyfluorinated carbon chains. These block co-polymers form micelles that can be loaded with oxygen and incorporated or introduced by various means or flows into scaffolds and/or tissues as an oxygen reservoir.

In one aspect, a block co-polymer is provided. The block co-polymer includes a water-soluble carrier block and an amino acid-based or acrylic acid-based block, with the amino acid-based or acrylic acid-based block including a fluorinated alkyl group or a fluorinated alkylene glycol group. Such block co-polymers are capable of entrapping oxygen in micelles which may then deliver the oxygen to a cell culture or tissue in vitro, ex vivo, or in vivo. In the micelle form, the water-soluble block is believed to form a shell-like structure around the fluorinated segments of the amino-acid- or acrylic-acid-based block, with the fluorinated segments trapping the oxygen.

The water-soluble carrier block includes groups that impart hydrophilic character to at least those blocks of the polymer. The blocks which are hydrophilic form the shell-like structure of the micelle. The water-soluble carrier block, does not render the entire polymer water-soluble, as the fluorinated groups are hydrophobic. Rather, the term water-soluble carrier block refers to a situation where a homopolymer of the block would be water-soluble. Groups which may form the water-soluble carrier block include, but are not limited to, a polyalkylene glycol group, a polyhydroxyacrylate, a polyhydroxymethacrylate, a poly(vinylpyrrolidone) group, a poly(2-methyl-2-oxazoline) group, a poly(2-ethyl-2-oxazoline) group, a poly(acrylamide) group, a polyethyleneimine group, or a co-polymeric group of any two or more such groups.

The amino acid- or acrylic acid-based block provides for attachment of the fluorinated moieties which are configured to trap oxygen when the polymer is formed into a micelle. Where it is an amino acid-based block, a chain of amino acids are formed, and side chains of the individual amino acids then provide functionality with which to attach fluorinated moieties. Where it is an acrylic acid-based block, the acrylic groups form the polymer backbone and amino acid side chains are introduced and which are further functionalized with the fluorinated moieties. Where the block is an amino acid-based block, illustrative groups that may form the block include, but are not limited to, amino acids having a side chain that may be further functionalized. For example, such groups include, α-glutamic acid groups, γ-glutamic acid groups, aspartic acid groups, tyrosine groups, serine groups, threonine groups, lysine groups, ornithine groups, histidine groups, N-(3-hydroxypropyl)aspartamide groups, or chains of any two or more such amino acid groups. Where the block is an acrylic acid-based block, it may include an acrylic acid group, methacrylic acid group, or co-polymer thereof. The amino acid- or acrylic acid-based block may also include a co-polymer of at least one amino acid group and at least one acrylic acid group. According to one embodiment, acrylic acid- or amino acid-based blocks may have up to about 5000 repeat units of either an amino acid, an acrylic acid, or a co-polymer block of amino and acrylic acids. In some embodiments, the block may have up to about 1000 repeat units.

The block co-polymers described above, may be generally represented by Formula I:

-[Block A-L-Block B]- (I).

In Formula I, Block A is the water soluble carrier block; Block B is the amino acid-based or acrylic acid-based block; and L is a linker group between Block A and Block B. The blocks may be segregated with Block A extending on one end of the polymer and Block B extending on the other end. Alternatively, the A and B blocks may be alternately or randomly located along the polymer backbone such that hydrophobic segments (i.e. the amino acid- or acrylic acid-based blocks) are interspersed with the hydrophilic segments (i.e. the water-soluble carrier blocks).

According to various embodiments, Block A includes hydrophilic groups. Hydrophilic groups are those groups that have an affinity for water. For example, hydrophilic groups tend to have oxygen or nitrogen, generally, or have ester, ether, carboxamide, carboxyl, hydroxyl or amine functionality. For example, and without limitation, Block A may include polyalkylene glycol groups, poly(vinylpyrrolidone) groups, poly(2-methyl-2-oxazoline) groups, poly(2-ethyl-2-oxazoline) groups, poly(acrylamide) groups, polyethyleneimine groups, or a co-polymeric group of any two or more such groups.

According to various embodiments, Block B includes amino acid- or acrylic acid-based groups having fluorinated moieties. The amino acids that can form Block B are those amino acids having a functional side chain. The functional side is then used to introduce fluorous groups, i.e. a fluorinated moiety. Where Block B is an amino acid-based block, illustrative groups that may form the block include, but are not limited to, α-glutamic acid groups, γ-glutamic acid groups, aspartic acid groups, tyrosine groups, serine groups, threonine groups, lysine groups, ornithine groups, histidine groups, N-(3-hydroxypropyl)aspartamide groups, or a co-polymer of any two or more such amino acid group. Where Block B is an acrylic acid-based block, it may include acrylic acid group, methacrylic acid group, or co-polymer thereof. Block B may also include a co-polymer of any two or more of the amino acid groups and acrylic acid groups.

The linker between Block A and Block B may be a bond or other functional linker group that attaches to both Block A and Block B. For example, and without limitation, linker L may be a bond, or L may include groups such as an alkylene; —O—; —C(O)—; —C(O)N($R^1$)($CH_2$)$_n$—; —N($R^2$)CO—; —C(O)O—; —C(O)O($CH_2$)$_n$—; —N($R^3$)C(O)O—; —N($R^4$)C(O)O($CH_2$)$_n$—; —OC(O)N($R^5$)($CH_2$)$_n$—; or N($R^6$)C(O)N($R^7$)($CH_2$)$_n$—. In such groups, $R^1$, $R^2$, $R^3$, $R^4$, $R^5$, $R^6$, and $R^7$ are each independently H or alkyl, and n is 0 or greater. In some embodiments, n is 0, 1, 2, 3, 4, or 5. Where L is a bond, an end group of Block A may bond directly to an end group of Block B, without a formal linker group between the blocks.

According to some embodiments, the polymer represented by Formula I may be represented by either Formula II or III. The polymers of Formulas II and III are:

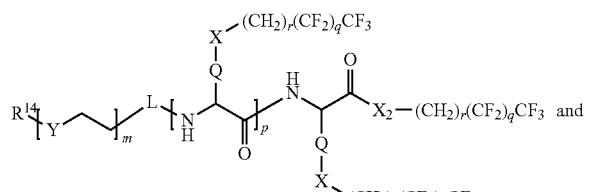

(Formula II)

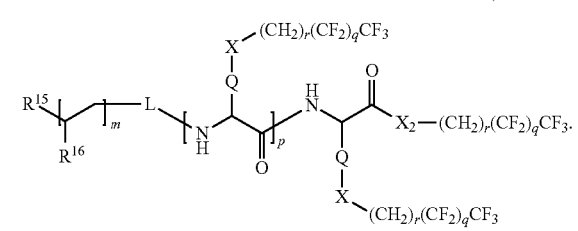

(Formula III)

In Formulas II and III, $R^{14}$ is H, alkyl, alkenyl, or a water-soluble group; $R^{15}$ and $R^{16}$ are individually water-soluble groups; Q is a glutamic acid side chain, a aspartic acid side chain, a tyrosine side chain, a serine side chain, a threonine side chain, a lysine side chain, a ornithine side chain, a histidine side chain, or an N-(3-hydroxypropyl)aspartamide side chain; Y is O, NH, or NC(O)alkyl; X is $CH_2$, O or $NR^{13}$; $R^{13}$ is H or alkyl; q is from 2 to 20; r is 0, 1, 2, or 3; and t is from 0 to 10. Repeat units denoted by m and p may be repeated throughout the polymer backbone. While no specific limitation is put on how many times the m and p units may be repeated, there are limits of practicality such that the polymers readily form micelles and neither the hydrophilic segments (i.e. Block A) or the hydrophobic segments (i.e. Block B) dominates to the detriment of the other for which it was designed. Accordingly, in one embodiment, m is from 1 to 1000; p is from 1 to 5000. In another embodiment, m is from 1 to 500 and p is from 1 to 1000. In some embodiments, Y is O, NH, or NC(O)($C_1$-$C_8$ alkyl). In some such embodiments, Y is O, NH, NC(O)$CH_3$, or NC(O)$CH_2CH_3$.

With regard to $R^{15}$ and $R^{16}$, as noted above, they are water-soluble groups that are oligomeric or polymeric. Such water soluble groups are well-known, and include amides, esters, pyrrolidones, carbonates, and the like. Illustrative water-soluble groups include, but are not limited to, groups such as pyrrolidone, C(O)$NH_2$, or C(O)$NR^{17}R^{18}$, where $R^{17}$ and $R^{18}$ are individually H or a $C_1$-$C_8$ alkyl. In some embodiments, $R^{14}$ is H or alkenyl; and $R^{15}$ and $R^{16}$ are each independently an alkylene glycol; a pyrrolidone, a oxazoline, a acrylamide, or an ethyleneimine. In other embodiments, $R^{14}$ is H or alkenyl; and $R^{15}$ and $R^{16}$ are both an alkylene glycol; a pyrrolidone, a oxazoline, a acrylamide, or an ethyleneimine.

With regard to Q, the groups on which Q are based are the amino acid side chain groups for glutamic acid, aspartic acid, tyrosine, serine, threonine, lysine, ornithine, histidine, or another amino acid group having a functional side chain. In the synthesis described below, the functional side chain then becomes the point of attachment for the fluorous groups. As used herein, "fluorous groups" are fluorinated alkyl groups which have an alkylene hydrocarbon spacer group. The general formula is —($CH_2$)$_r$($CF_2$)$_q$$CF_3$. The hydrocarbon spacer group isolates the electronegative fluorine groups to provide an electronically favorable reaction site through which the fluorous group is attached to the amino acid side chain.

As introduced above, the polymers may be used to prepare oxygenated micelles. While stirring vigorously, a suitably buffered aqueous solution is added slowly to a polymer dissolved in a suitable organic solvent such as tetrahydrofuran, dimethylformamide, methyl-ethyl-ketone or p-dioxane. The final polymer concentration is above its critical micelle concentration. Organic solvent and other small molecule impurities are removed by dialysis against distilled or buffered water with a membrane having particle size cutoff below the micelle diameter.

In another embodiment, the oxygenated micelles include any of the block co-polymers described above, molecular oxygen; and an aqueous vehicle. In some embodiments, the block co-polymer is represented by Formula I, II, or III. The micelles may include the molecular oxygen from about 0.5 vol % to about 50 vol %. The micelles may include the block co-polymer in the aqueous vehicle from about 0.5 wt % to about 50 wt % in the aqueous vehicle.

The micelles may include other additives such as, but not limited to, buffering agents, salts, surfactants, viscosity modifiers, stabilizers (against degradation due to freezing or contamination, for example), anti-freeze agents, diluents, encoding agents, and the like. Among such additives may be mentioned glycerin, dimethylsulfoxide, ethylene glycol, various gelatins both natural and synthetic, and polyols such as sorbitol. The aqueous vehicle may be buffered at a desired pH. For example, the pH may be at, or about 7. The aqueous vehicle may include sodium chloride at physiological saline concentration (e.g. 0.9 w/v % saline).

As introduced above, the polymers described herein are configured to entrap molecular oxygen in micellular form.

These micelles may then be used to deliver the oxygen to cells or tissue, in vitro, ex vivo, or in vivo, to aid in cell growth or viability, or to minimize or avoid hypoxia. Hypoxia may occur in tissue samples where oxygen cannot penetrate to the inner cells, during growth in tissue culture, ex vivo transplants, or after transplantation and before a blood supply is established. In some embodiments, engineered tissue may be perfused, grown, cultured or expanded with these oxygen-rich micelles prior to implantation. In addition to their use in oxygen delivery, micelles derived from the polymers can be designed for use as reservoirs to carry nutrients and growth factors such as VEGF to implanted tissues. Large molecular weight polymer blocks may form gels that could improve the oxygen releasing properties of the copolymer.

The micelles may be used to transport and deliver oxygen due to the structural properties of the polymers. The polymer will contain free carboxyl groups, i.e. carboxyl groups not bound in an ester or amide linkage to a perfluoroalkyl chain. Such free carboxyl groups are pH sensitive. In the relatively neutral pH of cultured cells undergoing active growth, micelles of the polymers and oxygen remain intact. However, upon the depletion of oxygen and/or nutrients, the pH of culture medium is reduced, resulting in protonation of the free carboxylate groups. The protonation induces conformational changes in the polymer leading to disruption of the micellar structure and controlled release of stored oxygen. Variation in the number of m and p groups, group Q, and group X, as well as the ratio of fluorocarbon-bound to free carboxyl groups permits optimization of the chemical composition of the polymers with regard to micellular properties. Specifically, the ease of micelle formation, micelle stability, oxygen carrying capacity, pH sensitivity of oxygen release from micelles, and improved survival of core cells in thick engineered tissue may all be modified. Higher molecular weight fluorocarbon containing block provides lower critical micelle concentration and supports ease of formation and stability of micelles. Oxygen carrying capacity is supported by increased proportion of fluorous groups in the core of the micelle. The presence of free carboxyl groups in the poly(amino acid) block supports sensitivity to low pH and oxygen release from micelles.

Such micelles may be used as perfusion or cell growth solutions. The micelles may also be used in maintaining and transplanting of complex cellular/tissue constructs; supplying devascularized organs with oxygen prior to transplantation; or oxygenating obstructed regions due to blockage, among others. For example, the micelles may be contacted with cardiac, hepatic, or renal tissue during transplantation when the tissue has been removed from a donor, during transportation, and until blood supplies are established within the recipient. Similarly, the micelles may be used as a cardioplegic solution additive for open heart surgery, as a blood substitute, an in vitro cell or tissue culture medium, a perfusion solution for myocardium or brain tissue in heart attacks and strokes, as a medium to increase the oxygenation of tumors consequently benefiting radiation and/or chemotherapy in cancer treatment, or a cardioplegic solution for open heart surgery.

In the in vitro culture of cells, tissues, and organs, the micelles may be used as a media supplement to increase the level of oxygenation. Cultured cells, tissues, and organs may be mammalian, non-mammalian, vertebrate, or invertebrate in origin. For example, the cells, tissues, and organs may be derived from humans, non-human primates, mice, rats, dogs, horses, chickens, fish, hamster, guinea pig, reptiles, insects, and the like. Any cell type may be cultured using the micelles, including cells derived from muscle, neural, connective, or epithelial tissue. Cultured cells may be immortalized cells, primary cells, tumor cells, chimeric cells, hybridomas, germline cells, somatic cells, stem cells, and the like.

Examples of primary cells that may be cultured using the micelles include but are not limited to chondrocytes, osteoblasts, epithelial cells, fibroblasts, myoblasts, neuroblasts, and the like. Illustrative cell lines that may be cultured using the micelles include but are not limited to BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, CHO cells, NS-1 cells, MRC-5 cells, WI-38 cells, BHK cells, 293 cells, 3T3 cells, and RK cells. Illustrative tissues that may be cultured using the micelles include but are not limited to epithelia, cornea, islet cells, bone marrow, heart valve, bone, cartilage, hepatic, and vascular tissue. Illustrative organs that may be cultured using the micelles include but are not limited to heart, kidney, liver, lungs, pancreas, intestine, and thymus. Cells, tissues, and organs may be cultured in vitro using media known in the art. Illustrative cell culture media include but are not limited to DMEM, DMEM/F12 media, Ham's F-10 media, Ham's F-12 media, medium 199, MEM, RPMI 1640 media, and others known in the art.

In some cases, cells, tissues, and organs may be cultured in vitro for purposes of transplantation. In some cases, the transplant will be an autograft, an allograft, an isograft, or a xenograft. Examples of cells, tissues, and organs that may be cultured in vitro for purposes of transplantation include but are not limited to epithelia, cornea, islet cells, bone marrow, heart valves, bone, cartilage, vascular tissue, heart, kidney, liver, lungs, pancreas, intestine, and thymus. In some cases, the transplant recipient will be a human subject. In some cases, the transplant recipient will be a non-human subject. In some cases the transplant recipient will be an intermediary host (or vessel) for a temporary duration.

Ample oxygen is required for tissue to regenerate after a traumatic event has occurred. Thus, the micelles may be used during the treatment of radiation damaged tissue, wounds, ischemia, vascular restriction, gas embolism/decompression sickness, tissue hypoxia, anemia, hemorrhagic or traumatic shock, ischemic brain edema, acute ischemia, polytrauma, or fat embolism.

Thus, the polymers may be used in methods of providing oxygen to tissues. Such methods include, contacting any of the above block co-polymers oxygen, forming oxygenated micelles in an aqueous environment; and contacting the oxygenated micelles with tissue.

The present technology, thus generally described, will be understood more readily by reference to the following Examples, which are provided by way of illustration and are not intended to be limiting of the present technology.

EXAMPLES

Example 1

Preparation of Compound 4, according to FIG. 1. Various monomethoxypoly(ethylene glycol)aldehydes (Compound 1; mPEG aldehyde; molecular weight=1,000, 2,000, 5,000, 10,000, 20,000 and 30,000 Daltons; Creative PEGWorks, Winston-Salem, N.C.) are reacted with various poly(L-glutamic acid)s (Compound 2; PGA; molecular weight range=750-5,000, 2,000-15,000, 15,000-50,000 and 50,000-100,000 Daltons; Sigma-Aldrich, St Louis, Mo.).

A mixture of the sodium salt of PGA (molecular weight range=2,000-15,000 Daltons, 5 mg/mL) and sodium cyanoborohydride (20 mM) in aqueous sodium acetate solution (100 mM, pH 5.0) is stirred in an ice bath. To this mixture is added Compound 1 (molecular weight=5,000 Daltons, 5 equivalents per mole of PGA). After stirring overnight at room temperature, Compound 3 is to be purified by dialysis against distilled water using a dialysis membrane (molecular weight cutoff=8,000). Freeze-drying provides Compound 3.

Various 1H,1H-perfluoroalkyl-1-alcohols ($C_5$ to $C_{18}$), 1H,1H,2H,2H-perfluoroalkyl-1-alcohols (C6 to C12), and 1H,1H-perfluoroalkyl-1-amines ($C_6$ to $C_{10}$) as well as 1H,1H,2H,2H-perfluoroalkyl-1-amine ($C_{10}$) from SynQuest Laboratories (Alachua, Fla.), the "fluorous group precursors," is then to be reacted with Compound 3. The fluorous group precursors are compounds having a perfluoroalkyl portion with an alkyl spacer portion. The fluorous precursors are then to be reacted with the free carboxyl groups of Compound 3.

A mixture of mPEG-PGA conjugate (Compound 3), a perfluoroalkyl amine or a perfluoroalkyl alcohol (1 mole equivalent per mole of free carboxyl), a base such as dimethaminopyridine (DMAP, 3 mole equivalents per mole of perfluoroalkyl amine or perfluoroalkyl alcohol), diisopropylcarbodiimide (DIPC, 1.3 mole equivalents per mole perfluoroalkyl amine or perfluoroalkyl alcohol), and dimethylformamide (DMF) is stirred for 1 to 2 days. After addition of aqueous sodium chloride solution (10%), the fluorinated block co-polymer (Compound 4) is obtained and purified by dialysis against distilled water using a dialysis membrane (molecular weight cutoff=8,000). Freeze-drying provides Compound 4.

Example 2

Preparation of micelles. As an amphiphilic block co-polymer having a hydrophilic block and a hydrophobic fluorocarbon block, Compound 4, forms micelles. These micelles exhibit a shell of PEG blocks on their outer surface exposed to the aqueous medium and a predominantly fluorous core capable of oxygen accumulation. Treatment of a mixture of Compound 4 and phosphate buffered saline (PBS; pH 7.4) with ultrasonic irradiation under high oxygen tension accumulates oxygen in newly forming micelles.

Example 3

Figure 2:
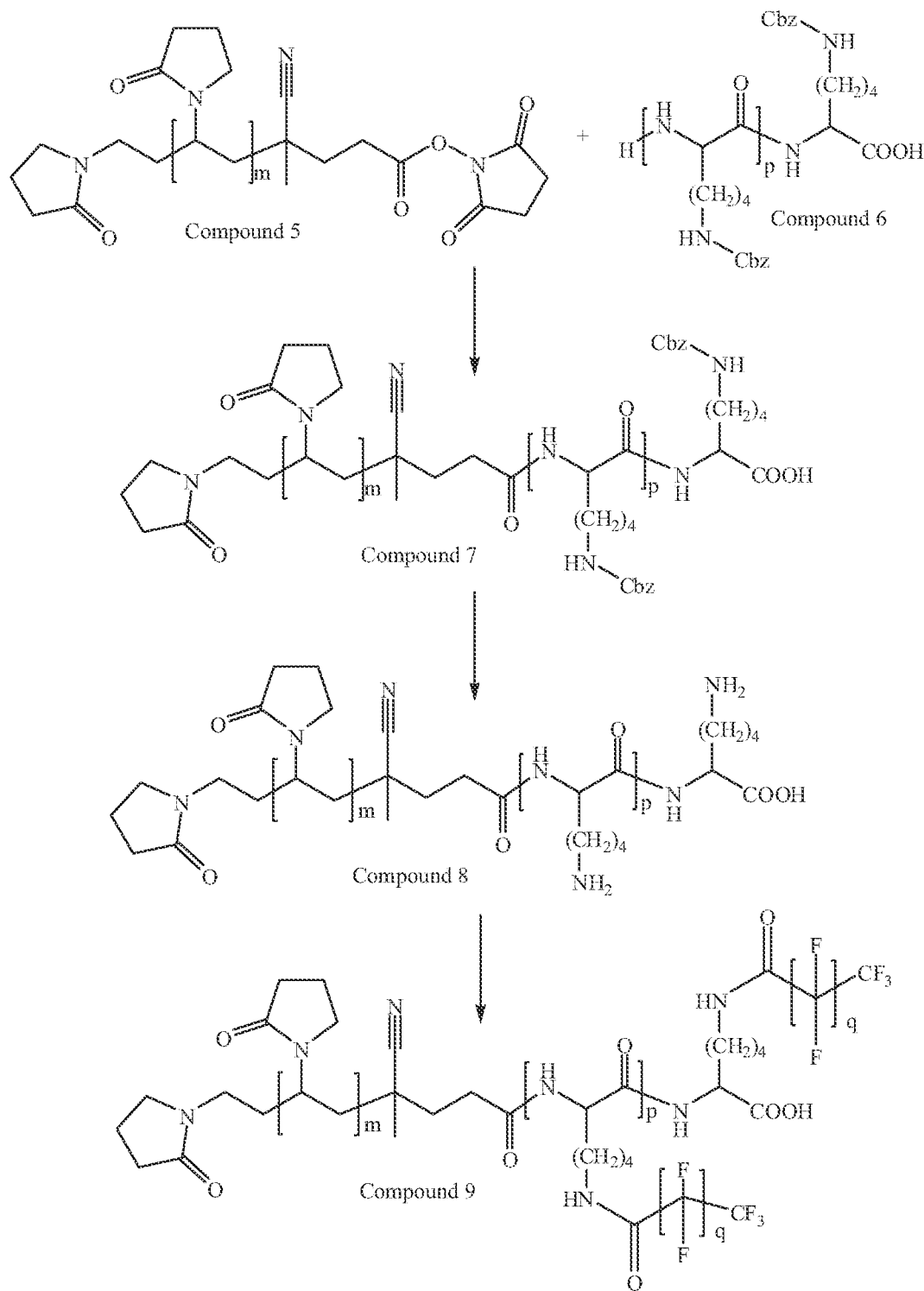
FIG. 2 is a schematic illustration of the synthesis of Compound 9, according to the examples.

Preparation of Compound 9 according to FIG. 2. Poly (vinylpyrrolidone) N-hydroxysuccinimides (Compound 5; number average molecular weight=2,000, 3,000, 5,800, 6,800, 15,200 Daltons) are to be synthesized according to a published method [Tsunoda, S, et al. *J. Controlled Release* 68, 335-341 (2000)].

A mixture of poly($\epsilon$-CBZ-L-lysine) (Compound 6; molecular weight range=1,000-4,000 Daltons; Sigma-Aldrich; CBZ is an abbreviation for benzyloxycarbonyl), Compound 5 (number average molecular weight=5,800; 5 equivalents per mole of Compound 6), and PBS (pH 7.4) is stirred at room temperature overnight. Compound 7 is purified by dialysis against distilled water using a dialysis membrane (molecular weight cutoff=6,000). Freeze-drying provides Compound 7.

A mixture of Compound 7, trifluoroacetic acid, and a 33% solution of hydrogen bromide in acetic acid (4 equivalents per mole of CBZ groups) is stirred at room temperature for 1 hour. After addition of excess diethyl ether, the precipitate is washed 3 times with diethyl ether and dried under reduced pressure to provide Compound 8.

Various perfluoroalkanoate esters ($C_6$ to $C_{16}$) from ABCR (Karlsruhe, Germany) may be reacted with the free lysine epsilon amino groups of Compound 8. A mixture of Compound 8, sodium methoxide (1 equivalent per mole of lysine epsilon amino group salt), methyl perfluorodecanoate (1 equivalent per mole of lysine epsilon amino group to be acylated), and methanol is heated under reflux for 24 hour. Volatiles are evaporated under reduced pressure and the solid is dried under reduced pressure to provide Compound 9.

Example 4

In vitro oxygenation. Engineered cardiac tissue is generated by adapting published methods [Stevens, K R, et al. *Proc Nat Acad Sci* 106, 16568-16573 (2009)]. A mixture of human embryonic stem cell (hESC) derived cardiomyocytes, umbilical vein endothelial cells (HUVECs), and embryonic fibroblasts (MEFs) are implanted into a suitable scaffold such as Matrigel and incubated in human EB medium. Oxygen-loaded fluorocarbon micelles (20% by weight) in medium are introduced by injection into the core of the scaffold. The scaffold with dispersed cells is incubated in medium, and the medium is to be replaced by fresh medium every two days until the cells permeate the scaffold. Also every two days, spent micelles are replaced in the scaffold core by slow syringe aspiration with fresh micelle/medium mixture.

Example 5

In vivo oxygenation. Sprague Dawley nude rats are to be anesthetized using isofluorane, intubated, and mechanically ventilated. The chest is opened, the pericardium is partially removed from the heart, the heart is scuffed slightly with a cotton swab, and the cell-laden scaffold from Example 4 is attached to the heart by using two to four sutures. Oxygen-loaded fluorocarbon micelles (20% by weight) in EB medium are introduced by syringe aspiration into the core of the scaffold. The chest is closed aseptically and animal recovery from surgery is monitored. Animals are administered cyclosporine A subcutaneously daily starting 1 day before and continuing for 7 days after scaffold implantation (0.75 mg/day). Animals are to then be killed 1 week after scaffold implantation. The hearts will be sectioned through the scaffold and examined by histology.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." Finally, as will be understood by one skilled in the art, a range includes each individual member.

Other embodiments are set forth in the following claims.

What is claimed is:

1. A block co-polymer of formula:

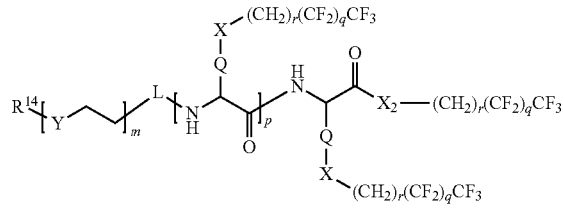

wherein:
$R^{14}$ is H, alkyl, alkenyl, or a water-soluble group;
Q comprises a glutamic acid side chain, a aspartic acid side chain, a tyrosine side chain, a serine side chain, a threonine side chain, a lysine side chain, a ornithine side chain, a histidine side chain, or an N-(3-hydroxypropyl) aspartamide side chain;
L is a bond; an alkylene; —O—; —C(O)—; —C(O)N($R^1$)($CH_2$)$_n$—; —N($R^2$)CO—; —C(O)O—; —C(O)O($CH_2$)$_n$—; —N($R^3$)C(O)O—; —N($R^4$)C(O)O($CH_2$)$_n$—; —OC(O)N($R^5$)($CH_2$)$_n$—; or N($R^6$)C(O)N($R^7$)($CH_2$)$_n$—;
$R^1$, $R^2$, $R^3$, $R^4$, $R^5$, $R^6$, and $R^7$ are each independently H or alkyl;
n is 0 or greater
Y is O, NH, or NC(O)alkyl;
X is $NR^{18}$;
$R^{18}$ is H or alkyl;
m and p are repeat block units in the polymer;
q is from 1 to 20;
and r is 0, 1, 2, or 3.

2. The block co-polymer of claim 1, wherein n is 0, 1, 2, 3, 4, or 5.

3. The block co-polymer of claim 1 wherein $R^{14}$ is H or an alkenyl.

4. A composition comprising oxygenated micelles comprising:
block co-polymer of claim 1;
molecular oxygen; and
an aqueous vehicle.

5. The composition of claim 4 comprising 0.5 vol % to about 50 vol % of the molecular oxygen.

6. The composition of claim 4, wherein the block copolymer comprises from about 0.5 wt % to about 50 wt % in the aqueous vehicle.

* * * * *

UNITED STATES PATENT AND TRADEMARK OFFICE
CERTIFICATE OF CORRECTION

| | | |
|---|---|---|
| PATENT NO. | : 8,691,284 B2 | Page 1 of 1 |
| APPLICATION NO. | : 13/443576 | |
| DATED | : April 8, 2014 | |
| INVENTOR(S) | : Klein et al. | |

It is certified that error appears in the above-identified patent and that said Letters Patent is hereby corrected as shown below:

On the title page, item (56), under "OTHER PUBLICATIONS", in Column 2, Line 32, delete "Enginnering," and insert -- Engineering, --, therefor.

In the Claims

In Column 12, Line 17, in Claim 1, delete "lvsine" and insert -- lysine --, therefor.

In Column 12, Line 39, in Claim 4, delete "block" and insert -- the block --, therefor.

Signed and Sealed this
Twenty-sixth Day of August, 2014

Michelle K. Lee
*Deputy Director of the United States Patent and Trademark Office*